(12) United States Patent
Gushchin et al.

(10) Patent No.: US 9,750,727 B2
(45) Date of Patent: Sep. 5, 2017

(54) TUBERCULOSIS DRUG BASED ON 4-THIOUREIDO-IMINOMETHYLPYRIDINIUM PERCHLORATE: METHOD OF PREPARATION AND TREATMENT

(71) Applicant: Joint Stock Company "Pharmasyntez", Irkutsk (RU)

(72) Inventors: Aleksander Sergeevich Gushchin, Irkutsk (RU); Tatiana Ivanovna Vinogradova, Tosno (RU); Petr Kazimirovich Yablonskiy, Saint Petersburg (RU); Gennady Andreevich Batyunin, Irkutsk (RU); Natalya Vyacheslavovna Zabolotnyh, Saint Petersburg (RU); Svetlana Nikolaevna Vasilieva, Saint Petersburg (RU); Alexey Vladimirovich Maligin, Irkutsk (RU)

(73) Assignee: Joint Stock Company "Pharmasyntez" (RU)

( * ) Notice: Subject to any disclaimer, the term of this patent is extended or adjusted under 35 U.S.C. 154(b) by 0 days.

(21) Appl. No.: 13/657,168

(22) Filed: Oct. 22, 2012

(65) Prior Publication Data
US 2013/0052265 A1 Feb. 28, 2013

Related U.S. Application Data

(63) Continuation of application No. PCT/IB2011/051566, filed on Apr. 12, 2011.

(30) Foreign Application Priority Data

Apr. 20, 2010 (RU) .................. 2010115705

(51) Int. Cl.
| | | |
|---|---|---|
| A61K 9/00 | (2006.01) |
| A61K 9/20 | (2006.01) |
| A61K 9/36 | (2006.01) |
| A61K 31/496 | (2006.01) |
| A61K 31/4425 | (2006.01) |
| A61K 9/02 | (2006.01) |
| A61K 9/28 | (2006.01) |
| A61K 9/48 | (2006.01) |
| A61K 9/50 | (2006.01) |
| A61K 31/133 | (2006.01) |
| A61K 31/395 | (2006.01) |
| A61K 31/438 | (2006.01) |
| A61K 31/4409 | (2006.01) |
| A61K 31/47 | (2006.01) |
| A61K 31/4965 | (2006.01) |
| A61K 31/7036 | (2006.01) |
| A61K 45/06 | (2006.01) |

(52) U.S. Cl.
CPC ........ *A61K 31/4425* (2013.01); *A61K 9/0095* (2013.01); *A61K 9/02* (2013.01); *A61K 9/2027* (2013.01); *A61K 9/2054* (2013.01); *A61K 9/2846* (2013.01); *A61K 9/4866* (2013.01); *A61K 9/5026* (2013.01); *A61K 31/133* (2013.01); *A61K 31/395* (2013.01); *A61K 31/438* (2013.01); *A61K 31/4409* (2013.01); *A61K 31/47* (2013.01); *A61K 31/4965* (2013.01); *A61K 31/7036* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 3,039,925 A * | 6/1962 | Domagk | ........ A61K 31/42 514/161 |
| 3,079,303 A * | 2/1963 | Raff et al. | ........ 424/500 |
| 2003/0152622 A1* | 8/2003 | Louie-Helm | ........ A61K 9/0065 424/468 |

FOREIGN PATENT DOCUMENTS

| | | |
|---|---|---|
| GB | 820196 A | 9/1959 |
| JP | 59046208 A | 3/1984 |
| RU | SU1621449 | 10/1996 |

(Continued)

OTHER PUBLICATIONS

Silveira J. et al., The Combination of Isoniaside (INH) + Isonicotinyladehyde-thiosemicarbaxone for Treatment of Pediatric Tuberculosis (Rio De Janeiro, Brazil) Sep. 1963 LNKD-PUBMED: 14112139, vol. 64, Sep. 196, pp. 561-586, XP 008144265, ISSN: 0018-5469.

Janssen G. et al., Investigation of the combination of isonicotinaldehyde and heterocyclicthiosemicarbazones. Monatsschrift Fur Kinderheilkunde, 1957, vol. 105, No. 7, 1957, pp. 258-261, XP 008144231, ISSN: 0026-9298.

Anonymous, Abstracts from the Literature. Journal of the American Medical Association, vol. 174, No. 18, Dec. 1960, pp. 2247-2258, XP 002661741, DOI: 10.1001/jama.1960.03030180067036, p. 2256, right-hand column.

(Continued)

*Primary Examiner* — Michael G Hartley
*Assistant Examiner* — Lance Rider
(74) *Attorney, Agent, or Firm* — Robert J. Varkonyi; Smith & Hopen, P.A.

(57) ABSTRACT

This invention relates to the field of chemical-pharmaceutical industry, specifically a new tuberculosis treatment that contains, as an active ingredient, 4-thioureido-iminomethylpyridinium perchlorate at a therapeutically effective and safe level and pharmaceutically acceptable excipients. In addition, this treatment relates to a method of the preparation of the new drug, providing a high yield of the new treatment. The new treatment has a higher tuberculostatic activity (200 times as high) and lower toxicity (2.4 times as low), as compared to a prototype drug, and is stable during long-term storage. This medicament may be used for treating and preventing all forms of pulmonary and extrapulmonary TB by using the new treatment in combination with other TB drugs.

15 Claims, 2 Drawing Sheets

(56) References Cited

FOREIGN PATENT DOCUMENTS

| RU | 2265014 C1 | 11/2005 |
| --- | --- | --- |
| RU | 2360905 C2 | 10/2009 |
| SU | 1621449 A1 | 10/1996 |
| SU | 961301 A1 | 10/2000 |
| WO | 02087547 A1 | 11/2002 |
| WO | WO 02087547 A1 * | 11/2002 |
| WO | WO2009004249 A2 * | 1/2009 |

OTHER PUBLICATIONS

Nosova E. V. et al., Synthesis and Tuberculostatic Activity of 1,7-Disubstituted Fluoroquinolone Acids. Actual Problems of Organic Chemistry. Novosibirsk 2003. Retrieved from the Internet: <URL: http: nioch.nsc.ru>school/03/file/124.pdf.
Manina G. et al., Decaprenylphosphoryl-B-D-ribose 2'-epimerase from Mycobacterium tuberculosis is a magic drug target. Curr Med Chem. 2010;17 (27) 3099-108 (abstract) [on-line] retrieved from PubMed, PMID: 20629622.
Supplemental International Search Report for International Application No. PCT/IB2011/051566, International filing date of Apr. 12, 2011, with a mailing date of Jul. 19, 2012.
International Search Report for International Application No. PCT/IB2011/051566, International filing date of Apr. 12, 2011, with a mailing date of Jan. 25, 2012.
International Preliminary Report on Patentability for International Application No. PCT/IB2011/051566, International filed of Apr. 12, 2011, with a date of completion of this report of Sep. 6, 2012.
Amidon et al., A Theoretical Basis for a Biopharmaceutic Drug Classification: The Correlation of in Vitro Drug Product Dissolution and in Vivo Bioavailability. Pharmaceutical Research. 1995. vol. 12 (No. 3): 413-420.
Wagner. Biopharmaceutics 21. Rate of Dissolution in Vitro and in Vivo: Part VI. Correlation of in Vivo with in Vitro Data—Theoretical and Practical Considerations. Drug Intelligence and Clinical Pharmacy. 1970. vol. 4: 160-163.
Fathima et al., Drug-excipient interaction and its importance in dosage form development. Journal of Applied Pharmaceutical Sciene. 2011. vol. 1 (No. 6): 66-71.
Warren et al., Chlorates and Perchlorates their manufacture, properties and uses. Navord Report 7147. 1960. vol. 1: 1-754.
Kramarenko. Toxiocological Chemistry. Higher School Headquarters Pub-S. 1989: 50-55.
Translation of Section 7 of Toxiocological Chemistry by Kramarenko: 1-6.
Isanaka, Sheila et al. Iron Deficiency and Anemia Predict Mortality in Patients with Tuberculosis 1-3. The Journal of Nutrition, 2011. 350-357.
Srinivasan, Asha et al. Perchlorate: Health Effects and Technologies for Its Removal from Water Resources. Int. J. Environ. Res. Public Health, 2009. 6, 1418-1442; doi:10.3390/ijerph6041418.
Van der Walt, Martha et al. Serious Treatment Related Adverse Drug Reactions amongst Anti-Retroviral Naive MDR-TB Patients. Open Access, 2013. vol. 8, Issue 4, e58817.
Schumacher, Perchlorates: their properties, manufacture and uses. Reinhold publishing corporation, N-Y, 1960, pp. 171-172.
Federal Facilities Forum Issue Paper "Perchlorate Treatment Technology Update", May 2005.
Bergqvist & De Maré, Hypothyroidism and cerebral edema following combined treatment of tuberculosis with Conteben (TBI69S) and p-amino-salicylic acid. Acta Med Scand. Aug. 5, 1952;143(5):323-5.
Gradmann, Re-inventing infectious disease: antibiotic resistance and drug development at the Bayer company 1945-80. Med Hist. Apr. 2016;60(2):155-180.
Pauser, et al., Roche: lifesaver for millions (2012 Roche, Basel).
Centers for Disease Control and Prevention. Treatment of Tuberculosis, American Thoracic Society, CDC, and Infectious Diseases Society of America. MMWR 2003;52(No. RR-11).
http://biology.tutorvista.com/biomolecules/carbohydrates.html, last accessed Jun. 22, 2016.
https://en.wikipedia.org/wiki/Cellulose, last accessed Jun. 22, 2016.
https://en.wikipedia.org/wiki/Starch, last accessed Jun. 22, 2016.
https://en.wikipedia.org/wiki/Sucrose, last accessed Jun. 22, 2016.
https://en.wikipedia.org/wiki/Cyclodextrin, last accessed Jun. 22, 2016.
Isoniazid. (Jan. 19, 2017). In Wikipedia, The Free Encyclopedia. Retrieved Feb. 13, 2017 from https://en.wikipedia.org/w/index.php?title=Isoniazid&oldid=760905711.

* cited by examiner

Fig. 1

| No. of group | Experimental conditions | Coefficient of organ weight | | | CFU level in the spleen | Index of lung damage | Mean index of prevalence | Mean ITE (%) |
|---|---|---|---|---|---|---|---|---|
| | | lungs | spleen | liver | | | | |
| 1 | 2 | 3 | 4 | 5 | 6 | 7 | 8 | 9 |
| 4<br>n=13 | Rifampicin<br>10 mg/kg, per os | 1.98±0.1 | 1.3±0.11 | 5.6±0.1 | 113.0±36.9 | 2.13±0.08 | 24.8 | - |
| 5<br>n=12 | New treatment,<br>20 mg/kg, per os +<br>rifampicin | 1.62±0.14<br>$p_{4-5}<0.05$ | 0.85±0.08<br>$p_{4-5}<0.01$ | 5.51±0.2 | 120.0±21.46 | 2.13±0.07 | 26.02 | - |
| | ITE (%) | +18.2 | +34.6 | +1.6 | -6.19 | 0 | - | +9.66 |
| 6<br>n=13 | Isoniazid,<br>10 mg/kg, s/c | 1.74±0.08 | 1.54±0.11 | 5.57±0.21 | 160.0±21.46 | 2.29±0.04 | 34.2 | - |
| 7<br>n=15 | New treatment + isoniazid | 1.58±0.12 | 1.3±0.13 | 5.37±0.19 | 120.0±21.46 | 1.92±0.06<br>$p_{7-6}<0.001$ | 26.0 | - |
| | ITE (%) | +9.2 | +15.6 | +3.6 | +25.0 | +16.1 | - | +13.9 |
| 8<br>n=12 | Rifabutin<br>8.5 mg/kg, per os | 1.37±0.09 | 1.02±0.07 | 5.37±0.14 | 61.5±12.1 | 1.48±0.09 | 14.1 | - |
| 9<br>n=11 | New treatment + rifabutin | 1.2±0.16 | 0.81±0.06<br>$p_{9-8}<0.05$ | 5.39±0.2 | 53.4±31.11 | 1.59±0.09 | 12.5 | - |
| | ITE (%) | +12.4 | +20.6 | -0.4 | +13.2 | -7.4 | - | +7.68 |
| 10<br>n=12 | Amycacin<br>20 mg/kg, s/c | 2.42±0.14 | 1.85±0.09 | 6.29±0.15 | 140.0±21.46 | 2.25±0.07 | 30.6± | - |

Fig. 2

| 1 | 2 | 3 | 4 | 5 | 6 | 7 | 8 | 9 |
|---|---|---|---|---|---|---|---|---|
| 11<br>n=12 | New treatment + amycacin | 2.08±0.21 | 1.21±0.07<br>$p_{11-10}<0.001$ | 5.89±0.19 | 140.0±21.46 | 2.21±0.12 | 30.3 | - |
| | ITE (%) | +14.0 | +34.6 | +6.3 | 0 | +1.8 | - | +11.34 |
| 12<br>n=7 | Ethambutol<br>20 mg/kg, per os | 3.27±0.38 | 3.08±0.57 | 8.08±0.52 | 180.0±21.46 | 2.48±0.08 | 39.4 | - |
| 13<br>n=12 | New treatment + ethambutol | 3.37±0.19 | 2.4±0.2 | 7.39±0.21 | 120.0±21.46 | 2.58±0.05 | 27.1 | - |
| | ITE (%) | -3.1 | +22.1 | +8.9 | +33.3 | -4.0 | - | +11.44 |
| 15<br>n=7 | Ofloxacin,<br>20 mg/kg, per os | 3.87±0.28 | 2.44±0.19 | 7.1±0.9 | 200.0±0 | 2.7±0.11 | 43.2 | - |
| 16<br>n=12 | New treatment + ofloxacin | 4.05±0.11 | 2.73±0.22 | 7.95±0.35 | 200.0±42.92 | 2.63±0.07 | 43.4 | - |
| | ITE (%) | -4.6 | -11.9 | -11.9 | 0 | -2.6 | - | -6.2 |

TUBERCULOSIS DRUG BASED ON 4-THIOUREIDO-IMINOMETHYLPYRIDINIUM PERCHLORATE: METHOD OF PREPARATION AND TREATMENT

FIELD OF THE INVENTION

This invention relates to the field of chemical-pharmaceutical industry, specifically a new antituberculous (TB) treatment that contains, as an active ingredient, 4-thioureido-iminomethylpyridinium perchlorate in a therapeutically effective and safe level and with pharmaceutically acceptable excipients. In addition, this new product relates to a method of preparation and a method of treating and preventing all forms of pulmonary and extrapulmonary TB by use in combination with other TB drugs.

BACKGROUND

The high mortality rate from TB is an urgent health issue. Globally, there were an estimated 9.27 million incident cases of TB in 2007, according to World Health Organization (WHO) data. This is an increase from 9.24 million cases in 2006, 8.3 million cases in 2000, and 6.6 million cases in 1990. Most of the estimated total cases in 2007 were in Asia (55%) and Africa (31%), with a small proportion in the Eastern Mediterranean (6%), Europe (5%), and the Americas (3%). The five top countries in terms of total incidence in 2007 were India (2.0 million), China (1.3 million), Indonesia (0.53 million), Nigeria (0.46 million), and South Africa (0.46 million). Of the 9.27 million incident cases, an estimated 1.37 million (15%) were HIV-positive; 79% of these HIV-positive cases were in the Africa and 11% were in South-East Asia.

Although the total number of incident cases of TB is increasing in absolute terms as a result of population growth, the number of cases per capita is falling. The rate of decline is slow, at less than 1% per year. Globally, rates peaked at 142 cases per 100,000 population in 2004. In 2007, there were an estimated 139 incident cases per 100,000 population. Incidence rates are falling in five of the six WHO regions (the exception is Europe, where rates are approximately stable).

There were an estimated 0.5 million cases of multidrug-resistant TB (MDR-TB). There are 27 countries (of which 15 are in Europe) that account for 85% of all such cases. The most prominent countries in terms of total numbers of MDR-TB cases are India (131,000), China (112,000), Russia (43,000), South Africa (16,000), and Bangladesh (15,000). By the end of 2008, 55 countries and territories had reported at least one case of extensively drug-resistant TB (XDR-TB) [World Health organization (WHO) Report 2009 [Guidelines for surveillance of drug resistance in tuberculosis. $4^{th}$ Ed. WHO/HTM/TB/2009.422, WHO Press, Geneva, CH].

Remarkable achievements in TB control are associated with drug treatments. There have already been a large number of such TB medications. The first chemical preparations (streptomycin, sodium para-aminosalicylate, and tibon) appeared at the end of 1940s. Then ftivazide, isoniazid, and new effective chemical preparations such as ethionamide, canamycin, florimycin, cycloserine, and prothionamide were developed, allowing the most appropriate and effective individual treatment. Then rifampicin, ethambutol, and mycobutin, which are very effective TB drugs, became available. However, *Mycobacterium tuberculosis* with extensive resistance to these new drugs then emerged.

In standard TB therapy (for all forms of TB), the basic and most effective TB drugs are isoniazid (isonicotinic acid hydrazide, INH) [M. D. Mashkovsky: Pharma Products, vol. 2, Kharkov, *Torsing*, 1997, p. 332-333, 341-342.], a forerunner of this new development, and rifampicin [M. D. Mashkovsky: Pharma Products, vol. 2, Kharkov, *Torsing*, 1997, p. 332-333, 341-342; A. G. Khomenko: Chemotherapy of Pulmonary Tuberculosis, Moscow: *Meditsina*, 1980, 279 p.]. Although isoniazid shows a good therapeutic effectiveness, it is very toxic ($LD_{50}$ is 150 mg/kg), and its long-term administration is associated with digestive, renal, emotional, hematological, and allergic disorders and toxic hepatitis. The main disadvantage of isoniazid is that resistance in *M. tuberculosis* is rapidly developed in 70% of patients and up to 30% of TB patients become chronic carriers. The semisynthetic antibiotic rifampicin is also very active against *M. tuberculosis*, although it has high toxic effects. As with isoniazid, the main disadvantage of rifampicin is a rapid development of rifampicin resistance in *M. tuberculosis*, which is observed in 40-50% of TB patients and significantly decreases the drug's effectiveness. In cases of rifampicin-resistant TB, it is necessary to combine rifampicin with other TB drugs (streptomycin, isoniazid, ethambutol, etc.) [M. D. Mashkovsky: Pharma Products, vol. 2, Kharkov, *Torsing*, 1997, p. 332-333, 341-342]. Resistance of *M. tuberculosis* to available TB drugs necessitated the development of new types of treatment and their combination.

The object of the new preparation outlined here is to prepare a new highly effective TB treatment that has minimal toxic effects and is stable during storage.

SUMMARY OF THE INVENTION

The medicament is a new original TB treatment that contains, as an active ingredient, 4-thioureido-iminomethylpyridinium perchlorate in a therapeutically effective and safe level and pharmaceutically acceptable excipients.

The 4-thioureido-iminomethylpyridinium perchlorate is obtained by reacting (excess) 4-pyridine aldehyde with thiosemicarbazide in water-ethanol solutions of 48-55% perchloric acid at 80-85° C.

The TB drug contains an active ingredient 4-thioureido-iminomethylpyridinium perchlorate 5.0-90.0% w/w and pharmaceutically acceptable auxiliary substances 100% w/w (% expressed by weight of the total formulation).

The effective amount of active ingredient in the formulation is 5 to 1,000 mg.

The medicament preferably contains at least one more additional TB agent to produce a synergic effect. Exemplary additional TB agents include active ingredients such as isoniazid, pyrazinamid, rifampicin, rifabutin, amycacin, ethambutol, and fluoroquinolone antibiotic or their combinations.

Preparation preferably may be in the form of film-coated tablets (enteric coated modified release tablets), or combined tablets, capsules, granules, suppositories, and suspensions. The pharmaceutical dosage form of the present invention may be prepared using conventional technologies [Pharmaceutical Technology. Dosage Form technology, $2^{nd}$ ed., Moscow, 2006].

Administration may be oral or parenteral. The dose of the medication depends on the patient's age, condition and weight and the route of administration.

In addition to the active ingredient, the medicine may contain excipients such as binders, bulking materials, preservatives, glidants, softeners, humectants, dispersants, emulsifiers, diluents, antioxidants and/or propellants and prolongators [Sucker et al.: Pharmazeutische Technologie, *Thieme-Verlag*, Stuttgart, 1991].

The target additives are preferably sucrose, povidone, microcrystalline cellulose, colloidal silicon dioxide, ethylcellulose, copolymers of methacrylic acid and ethyl acrylate, triethyl citrate, macragol, talc, and ferric oxide dye, in amounts expressed as percent by weight of the active ingredient:

Sucrose: 3.1-50.4
Povidone: 0.9-14.4
Microcrystalline cellulose: 1.1-18.0
Colloidal silicon dioxide: 0.2-3.6
Ethylcellulose: 0.2-3.6

The most common techniques for the preparation of tablets are three technological processes: wet granulation, dry granulation, and direct compression.

However, described herein is a novel formulation based on the 4-compound. The methods for preparing the novel composition using the steps described herein are not disclosed in the prior art.

For this the optimum technique is the wet granulation procedure, including mixing, wetting, granulation, drying, dusting, and tabletting [Dosage Form technology, Ed. L. A. Ivanova, Moscow: *Meditsina*, 1991, vol. 2, p. 142, 223.].

The method involves the following steps:
(a) Powders of 4-thioureido-iminomethylpyridinium perchlorate, colloidal silicon dioxide, crosspovidone, magnesium stearate, povidone, microcrystalline cellulose, hypromellose (hydroxypropyl methylcellulose), talc, polyethylene glycol, propylene glycol, titanium dioxide, and yellow ferric oxide are independently sifted through sieves;
(b) To prepare a humectant, purified cold water (either deionized or distilled) and povidone are put into a reactor and mixed for 30 min at 60° C. until a clear homogenous solution of light-yellow colour is obtained;
(c) To prepare the mass for tabletting, 4-thioureido-iminomethylpyridinium perchlorate and microcrystalline cellulose are mixed for 15 min, then the humectant is added and mixed for at least 15 min until a uniform homogenous mass is obtained;
(d) The mass obtained at step (c) is subjected to wet granulation, such as low-shear granulation, high-shear granulation and fluid bed granulation;
(e) The wet granulated material obtained at the stages (d) is dried for 20 min at 0.2 mPa and 55±2° C. until the residual moisture content is 1.0-2.0%;
(f) The dried granulated material obtained at step (e) is subjected to dusting and dry granulation, wherein it is placed into a vibrosieve hopper and then with an antiadherent (aerosil, crosspovidone, magnesium stearate) put into a mixer, avoiding dust generation, and mixed for 15 min to obtain mass for tabletting;
(g) The mass for tabletting obtained at step (f) is compressed in a tablet press;
(h) Tablet cores are coated with aqueous suspension comprising a hypromellose mixture, yellow ferric oxide, macrogol, talc, propylene glycol, and titanium dioxide to obtain the final product.

The final tablets are oval, biconvex, and coated with yellow to dark yellow film.

When broken, the fracture zone of each tablet is of a light yellow to green-yellow colour.

The drug yield is 99.47%. Using this method, it is possible to obtain the maximum such yield.

A second method for the preparation of the new TB treatment is also proposed.

This involves direct compression and wet granulation procedures, including mixing, wetting, granulation, rolling until a desired size, coating, and drying [Dosage Form technology, Ed. L. A. Ivanova, Moscow: *Meditsina*, 1991, vol. 2, p. 142, 223].

In this 4-thioureido-iminomethylpyridinium perchlorate is combined with colloidal silicon dioxide, microcrystalline cellulose, and ethylcellulose; the mixed material mixed with aqueous solution of 3.0-5.0% povidone and 30.0-35.0% sugar syrup; granulated; and rolled. The granules are dried at 40-45° C. until the residual moisture content is 1.5-4.5%.

The granule cores are coated using an established technique, wherein a 20% aqueous solution of methacrylic acid-ethyl acrylate copolymers and pigment suspension of talc and ferric oxide are used.

A method for treating and preventing all forms of pulmonary and extrapulmonary TB in combination with other TB drugs is detailed in the new medicine outlined here.

Under this treatment regimen of 4-thioureido-iminomethylpyridinium perchlorate without excipients, the drugs may be administered by oral or parenteral (subcutaneously, intravenously, intramuscularly, intraperitoneally) at a single daily dose of 20 mg/kg (1,200 mg/kg), with maximum single dose of 30 mg/kg (1,800 mg/day).

To slow the development of drug resistance in *M. tuberculosis*, the drug is prescribed together with other TB drugs or their combinations (isoniazid, pyrazinomide, rifampicin, rifabutin, amycacin, ethambutol, fluoroquinolone antibiotics).

Biological Activity of the New Treatment
Materials and Methods for Studying Antituberculosis Activity of the New Treatment
1. Assessment of In Vitro Activity (Cultures of Microorganisms and Methods)

The following strains of microorganisms were used:
1) Laboratory test strains from *Mycobacterium tuberculosis* complex, which are obtained from Tarasevich State Scientific Research Institution for Standardization and Control of Biomedical Preparations and are sensitive to the current TB drugs:

*M. tuberculosis* Erdman;
   *M. tuberculosis* H37Rv;
   *M. tuberculosis* "Academia";
   *M. bovis bovinus* 8;

2) Cultures with multiple drug resistance isolated from patients with newly diagnosed TB (14 strains):

no. 5419 StPIP[1], resistant to isoniazid (10 µg/ml), rifampicin (40 µg/ml), and streptomycin (50 µg/ml);

[1] StPIP=St. Petersburg Institute of Phthisiopulmonology no. 2483 StPIP, resistant to isoniazid (1 µg/ml), rifampicin (40 µg/ml), streptomycin (5 and 10 µg/ml), rifabutin (40 µg/ml), ethambutol (2 µg/ml);

no. 3485 and no. 3589 StPIP, resistant to isoniazid (1 µg/ml), rifampicin (20 and 50 µg/ml), streptomycin (50 µg/ml), canamycin (30 µg/ml), ethambutol (2 µg/ml), ethionamid (30 µg/ml);

no. 3019 StPIP, resistant to isoniazid (1 [[и]] and 25 µg/ml), rifampicin (20 and 50 µg/ml), streptomycin and canamycin (30 and 50 µg/ml, respectively), ethionamid (30 µg/ml);

no. 3655 StPIP, resistant to isoniazid (1 µg/ml), rifampicin (20 and 50 µg/ml), streptomycin (50 µg/ml), canamycin and ethambutol (30 µg/ml);

no. 3689 StPIP, resistant to isoniazid (1 µg/ml), rifampicin (20 and 50 µg/ml), streptomycin (50 µg/ml), canamycin (30 µg/ml);

no. 3910 StPIP, resistant to isoniazid (1 µg/ml), rifampicin (20 and 50 µg/ml), streptomycin (50 µg/ml), canamycin and ethionamid (30 µg/ml);

no. 1201 StPIP, resistant to isoniazid (1 µg/ml), rifampicin (20 µg/ml), streptomycin (50 µg/ml), canamycin (30 µg/ml), ethambutol (2 µg/ml);

no. 41 and no. 779 StPIP, resistant to isoniazid (1 µg/ml), rifampicin (20 and 50 µg/ml), streptomycin (50 µg/ml);

no. 1081 StPIP, resistant to rifampicin (20 µg/ml), streptomycin (50 µg/ml);

no. 1719 and no. 1279 StPIP, resistant to isoniazid (1 µg/ml), rifampicin (20 µg/ml), streptomycin (50 µg/ml), canamycin and ethionamid (30 µg/ml);

3) Nonspecific microorganisms sensitive to antimicrobial preparations (from collection of StPIP, Roszdrav):

gram-negative bacilli: *E. coli;* gram-positive cocci: *Staphylococcus aureus, Streptococcus aureus, Corynebacterium pseudodiphtericum* (diphtheroid).

The antimicrobial activity of 4-thioureido-iminomethyl-pyridinium perchlorate was studied using a common method of double serial dilution in nutrient media depending on the biological properties of the test strains:

Soton's synthetic medium with 10% normal serum (for mycobacteria);

sugar broth (for gram-positive and gram-negative bacteria).

Microbial suspension was prepared ex tempore at working concentration of $5\times10^6$ cells/ml.

The 4-thioureido-iminomethylpyridinium perchlorate doses were studied in range of 100-0.19 µg/ml (without excipient), and 3 repeated tests were performed for each culture. A 0.2 ml sample of suspension of test strains was added to each test and control tubes: a surface plating method was used for mycobacterial suspension, and a deep plating method was used for suspension of nonspecific bacteria. The nonspecific bacterial growth and mycobacterial growth were measured following 24 h and 7-10 days, respectively. The criterion of activity was the lowest concentration of the new treatment in the media to completely inhibit bacterial growth (minimal inhibitory concentration, MIC, µg/ml).

The strain *M. bovis bovinus* 8 sensitive to TB drugs was used in experimental models of tuberculosis.

2. Assessment of Therapeutic Effect of the New Treatment.

For this purpose, the index of treatment effectiveness (ITE) (%) was used. The ITE is relative change, which involves comparing the severity of TB infection in control groups and in animals receiving the new treatment. It is calculated by the following formula:

$$ITE(\%) = \frac{n_c - n_t}{n_c} \times 100,$$

where $n_c$ and $n_t$ are the mean values in the control and test groups, respectively.

The positive ITE (plus-effect) indicates either a decrease in prevalence or an increase in therapeutic activity of TB drugs combined with the new treatment.

The negative ITE (minus-effect) indicates either an increase in prevalence or a decrease in therapeutic activity of the TB drug combined with the new treatment.

When assessing the activity of comparator drugs, the ITE was calculated in a similar way and was designated using common symbols (first letter of the drug name).

The degree of relationships in variations of therapeutic effects was measured using the rank correlation coefficient (r) and regression coefficient of Y and X. For this purpose, the Student-Fisher methods were used.

2. Antimicrobial Activity In Vitro of the New Treatment

Data on the effect of the new treatment on the growth of test strains from *Mycobacterium tuberculosis* complex, which are sensitive to the current TB drugs, are given in Table 1.

TABLE 1

Effect of the new treatment on the growth of drug-sensitive test strains of mycobacteria (mycobacterial suspension density is $10^6$ cells/ml)

| Concentration of the new treatment in medium (μg/ml) | Degree of mycobacterial growth | | | |
|---|---|---|---|---|
| | *M. bovis* bovinus 8 | *M. tuberculosis* H37RV | *M. tuberculosis* Erdman | *M. tuberculosis* "Academia" |
| 100 | --- | --- | --- | --- |
| 50 | --- | --- | --- | --- |
| 25 | --- | --- | --- | --- |
| 12.5 | --- | --- | --- | --- |
| 6.25 | --- | --- | --- | --- |
| 3.125 | --- | ++ | --- | ++ |
| 1.56 | --- | +++ | + | +++ |
| 0.78 | + | +++ | ++ | +++ |
| 0.39 | ++ | +++ | ++ | +++ |
| 0.19 | ++ | +++ | ++ | +++ |
| Culture control | +++ | +++ | +++ | +++ |

As can be seen from Table 1, the new treatment inhibited the growth of the test strains at concentration ranging from 1.56 μg/ml to 6.25 μg/ml. The drug showed the highest inhibiting activity against *M. bovis bovinus* 8. The primary inhibition of mycobacterial growth (++) was detected at concentration of 0.19 μg/ml; and complete inhibition (MIC), at concentration of 1.56 μg/ml. The following strains are given in descending order of inhibitory effect:

*M. tuberculosis* Erdman (MIC=3.125 μg/ml)

*M. tuberculosis* H37RV and *M. tuberculosis* "Academia" (MIC=6.25 μg/ml)

The activity of 4-thioureido-iminomethylpyridinium perchlorate against gram-positive cocci (*Staphylococcus aureus, Streptococcus* aureus) and gram-positive and gram-negative bacilli (*E. coli* and diphtheroid) was studied to determine the range of antimicrobial activity of 4-thioureido-iminomethylpyridinium perchlorate. The results of the study are given in Table 2.

TABLE 2

Effect of the new treatment on the growth test strains of gram (+) and gram (−) microorganisms (microbial suspension density is $10^6$ cells/ml)

| Concentration of the new treatment in medium (μg/ml) | Degree of the growth of test strains | | | |
|---|---|---|---|---|
| | *Staphyl. aureus* | *Strept. aureus* | *E. coli* | Diphtheroid |
| 100 | +++ | +++ | +++ | +++ |
| 50 | +++ | +++ | +++ | +++ |
| 25 | +++ | +++ | +++ | +++ |
| 12.5 | +++ | +++ | +++ | +++ |
| 6.25 | +++ | +++ | +++ | +++ |
| 3.125 | +++ | +++ | +++ | +++ |
| 1.56 | +++ | +++ | +++ | +++ |
| 0.78 | +++ | +++ | +++ | +++ |
| 0.39 | +++ | +++ | +++ | +++ |

TABLE 2-continued

Effect of the new treatment on the growth test strains of gram (+) and gram (−) microorganisms (microbial suspension density is $10^6$ cells/ml)

| Concentration of the new treatment in medium (μg/ml) | Degree of the growth of test strains | | | |
|---|---|---|---|---|
| | Staphyl. aureus | Strept. aureus | E. coli | Diphtheroid |
| 0.19 | +++ | +++ | +++ | +++ |
| Culture control | +++ | +++ | +++ | +++ |

As can be seen from Table 2, even at high concentrations (100 μg/ml) in the medium, the new treatment did not affect the growth of gram-positive and gram-negative microorganisms.

The inhibiting activity of the new treatment against drug-sensitive mycobacteria was studied in 14 clinical isolates, of which 2 (14.3%) isolates were resistant to 6 TB drugs, 7 (50%) to 5 TB drugs, 1 (7.1%) to 4 TB drugs, 3 (21.4%) to 3 TB drugs, and 1 (7.1%) to 2 TB drugs (see Table 3).

TABLE 3

Effect of the new treatment on the growth of drug-resistant clinical isolates of M. tuberculosis (mycobacterial suspension density is $5 \times 10^6$ microbial cells/ml)

| Test isolates of M. tuberculosis | Minimal inhibitory concentration (MIC, μg/ml) of 4-thioureido-iminomethylpyridinium perchlorate (without excipient) |
|---|---|
| Resistant to 6 TB drugs no. N3485 | 6.25 |
| Resistant to 6 TB drugs no 3589 | 6.25 |
| Resistant to 5 TB drugs no 2485 | 50 |
| Resistant to 5 TB drugs no 1201 | 6.25 |
| Resistant to 5 TB drugs no 3019 | 3.125 |
| Resistant to 5 TB drugs no 3655 | 3.125 |
| Resistant to 5 TB drugs no 3910 | 3.125 |
| Resistant to 5 TB drugs no 1719 | 3.125 |
| Resistant to 5 TB drugs no 1279 | 3.125 |
| Resistant to 4 TB drugs no 3689 | 6.25 |
| Resistant to 3 TB drugs no 5419 | 3.125 |
| Resistant to 3 TB drugs no 779 | 1.56 |
| Resistant to 3 TB drugs no 41 | 3.125 |
| Resistant to 2 TB drugs no 1081 | 1.56 |

The tests showed that the new treatment inhibited the growth of all drug-resistant clinical isolates:
  14.3% (2 strains)—at a dose of 1.56 μg/ml;
  50.0% (7 strains)—at a dose of 3.125 μg/ml;
  28.6% (4 strains)—at a dose of 6.25 μg/ml;
  7.1% (1 strain)—at a dose of 50.0 μg/ml.

Notably, the new treatment was effective against strains resistant to 5-6 TB drugs, where MIC for 88.8% of cultures was 3.125-6.25 μg/ml.

Thus, in vitro studies showed that the new treatment:
  showed a selective antimicrobial activity only against M. tuberculosis;
  had a marked antituberculosis activity against both drug-sensitive and drug-resistant strains of M. tuberculosis.

1.2 Effectiveness of the New Treatment Used as Monotherapy in Experimental Tuberculosis in Mice The study was performed in 200 white non-breed male mice weighing 18 to 20 g. In these mice, the strain M. bovis bovinus 8 caused a clinical picture of generalized tuberculosis, and specific foci of inflammation were visualized on day 11 after infection. Beginning from this day, the drugs studied were administered to the test animals.

On day 52 after infection, the fatality rate in the control group (infected animals without treatment) was 95.8% (Table 4).

At a dose of 10, 20, and 30 mg/kg the new treatment reduced lethality by 31.6%, 73.9%, and 97.5%, respectively (Table 4). The protective effect of the drug was also seen in reducing the weight loss in infected mice. At a dose of 10, 20, and 30 mg/kg the drug decreased the weight loss by 5.3%, 21.5%, and 19.0%, respectively (Table 4).

TABLE 4

Protective effect of the new treatment, as measured by lethality rate and changes in body weight in mice infected with M. bovis bovinus 8

| No. of group | Experimental conditions | Lethality | | Body weight | |
|---|---|---|---|---|---|
| | | % | ITE % | % of initial | ITE % |
| 2 | Infected animals without treatment n = 24 | 95.8 | 0 | 77.8 | 0 |
| 3 | New treatment 10 mg/kg, per os, per day n = 16 | 62.5 | +31.6 | 81.9 | +5.3 |
| 4 | New treatment 20 mg/kg, per os, per day n = 16 | 25.0 | +73.9 | 94.5 | +21.5 |
| 5 | New treatment 30 mg/kg, per os, per day n = 16 | 2.4 | +97.5 | 92.6 | +19.0 |

Note:
ITE = index of treatment effectiveness

Thus the high protective and therapeutic characteristics of the drug used as monotherapy in mice with experimental tuberculosis indicate that it can be regarded an effective antimycobacterial remedy. These results are in line with capacity of the drug to inhibit in vitro growth of the strain M. bovis bovinus 8 (Table 1).

Effectiveness of the New Treatment Used as Monotherapy in Experimental Tuberculosis in Rabbits The study was performed in 18 male chinchilla rabbits infected with M. bovis bovinus 8 in marginal auricular veins. Beginning from the day of infection, the new treatment was administered to rabbits (n=6) per os at a dose of 20 mg/kg for 2 months. Groups for comparison: infected rabbits without treatment (infection control, n=6) and infected rabbits treated with isoniazid (15 mg/kg, per os, n=6). The results of experiment are given in Table 5.

TABLE 5

Protective effect of the new treatment, as measured by lethality rate and changes in body weight in rabbits infected with M. bovis bovinus 8

| No. of group | Experimental conditions | Lethality | | Body weight | |
|---|---|---|---|---|---|
| | | % of initial number | ITE (%) | % of initial | ITE (%) |
| 1. | Infection control n = 6 | 100 | 0 | −27.6 | — |
| 2. | Isoniazid 15 mg/kg per os n = 6 | 0 | +100.0 | −6.99 | +74.67 |
| 3. | New treatment 20 mg/kg per os, n = 6 | 0 | +100.0 | −7.13 | +77.17 |

As can be seen from Table 5, the drug, compared to isoniazid, was more effective in preventing rabbit death from TB infection and in increasing their body weight (on average by 77.17% versus 74.67%).

2.1. Effect of the New Treatment on the Therapy of TB Drugs in Experimental Tuberculosis in Mice The study was performed in 250 white non-breed male mice. Six combinations were compared of the new treatment (20 mg/kg, per os) with TB drugs of different specific activity. Treatment groups received monotherapy with the test TB drugs at mean therapeutic doses. In all groups, treatment was started on day 12 after infection, when specific inflammatory changes in lungs were confirmed by autopsy in mice from the infection control group. The results were assessed following 42 days (6 weeks) of treatment.

The effect of the new treatment on the therapeutic effectiveness of TB drugs, as measured by the severity of organ damage, varied depending on the properties of the test drugs (FIGS. 1 and 2). TB drugs were divided into 3 groups depending on interactions with the new treatment.

Group 1. TB Drugs Having Synergic Interactions with the New Treatment (Increased Therapeutic Effectiveness Reflected by Indices of Organ Damage):

Isoniazid: Therapeutic effectiveness was increased on average by 13.9%, varying from 3.6% (a decrease in the coefficient of liver weight) to 25% (a decrease in CFU levels in the spleen);

Amycacin: Therapeutic effectiveness was increased on average by 11.34%, varying from 34.6% (a decrease in the coefficient of liver weight, $p<0.001$) to 1.8% (a decrease in the index of lung damage).

Group 2. TB Drugs Providing Increased Therapeutic Effectiveness, as Measured by Most Indices of Organ Damage (Three of Five):

Rifampicin: Therapeutic effectiveness was increased by 9.66% owing to a decrease in coefficients of lung (by 18.2%, $p<0.05$), spleen (by 34.6%, $p<0.01$), and liver (by 1.6%) weights, although with an increase in CFU levels by 6.19%;

Rifabutin: Therapeutic effectiveness was increased by 7.68% owing to a decrease in coefficients of lung (by 12.4%) and spleen (by 20.6%, $p<0.05$) weights and in isolation rates of M. tuberculosis, although with an increase in both the coefficient of liver weight and the index of lung damage (by 0.4% and 7.4%, respectively);

Ethambutol: Therapeutic effectiveness was increased by 11.44% owing to a decrease in coefficients of spleen (by 22.1%) and liver (8.9%) weights and in CFU levels in the spleen (by 33.3%), although with an increase in both the index of lung damage and the index of lung weight (by 4.0 and 3.1%, respectively).

Group 3. TB Drugs Acting with the New Treatment in an Antagonistic Way:

Ofloxacin: Therapeutic effectiveness was decreased by 6.2%, with a decrease in indices varying from 4.65% to 11.9%, except for an increase in the index of lung damage by 2.6%.

The phagocytic activity of peritoneal macrophages (pMP) in the test groups is given in Table 7. As can be seen from this table, the mean macrophagal activity of pMP during monotherapy with the new treatment was similar to that in the intact mice (132.41 versus 154.97). The new treatment activated those drugs which decreased the effectiveness of phagocytosis during monotherapy. Phagocytosis was activated when the new drug was used in combination with rifampicin (1.4-fold increase, from 71.43 to 99.12), rifabutin (1.3-fold increase, from 66.88 to 83.55), and ofloxacin (1.2-fold increase, from 95.14 to 111.66). The pMP activity was decreased when the new drug was used in combination with isoniazid (1.2-fold decrease, from 77.66 to 66.54), ethambutol (1.3-fold decrease, from 106.35 to 81.95), and amycacin (2.8-fold decrease, from 193.42 to 68.29).

Morphological indices obtained for six TB drugs, which were used as monotherapy and in combination with the new treatment, are given in Table 7. The latter, when combined with rifampicin, isoniazid, ofloxacin, ethambutol, and amycacin, improved the indices of lung damage by 16.9, 10.1, 3.24, 3.19, and 2.56%, respectively. The index of lung damage was increased (by 15.9%) only when the new treatment was used in combination with rifabutin.

TB drug classification depending on the therapeutic effectiveness of these drugs used in combination with the new treatment, as measured by the comprehensive tests using correlation analysis, is given in Table 8. There were three combinations with maximum positive effect in seven damage tests (20 cases). Of these combinations, the leading combinations were rifabutin+the new treatment and rifampicin+the new treatment (each in 7 cases). Less frequent combinations were amycacin+the new treatment (4 cases) and isoniazid+the new treatment (2 cases). A weak therapeutic effectiveness was observed for the combination of the new treatment with ofloxacin or ethambutol.

TABLE 7

Effect of the new treatment on the activity of TB drugs, as measured by morphological activity

| | | Scored sum of area | | | | |
|---|---|---|---|---|---|---|
| No. of group | Drug | Breathing lung tissue | Dense lymphocytic infiltrate | Desquamative pneumonia | Polymorpho cellular infiltrate | Total lung tissue |
| 4 | Rifampicin | 19.65 | 2.37 | 1.94 | 0 | 23.96 |
| 5 | Rifampicin + new treatment | 17.9 | 3.63 | 2.7 | 0 | 24.23 |
| | % ITE | −8.9 | +53.1 | +39.2 | 0 | +1.1 |
| 8 | Rifabutin | 23.27 | 0.53 | 0.16 | 0 | 23.96 |
| 9 | Rifabutin + new treatment | 23.24 | 0.64 | 0 | 0 | 23.88 |
| | % ITE | −0.13 | +20.7 | −100.0 | — | — |
| 6 | Isoniazid | 17.5 | 1.59 | 3.52 | 0.86 | 23.47 |
| 7 | Isoniazid + new treatment | 19.23 | 3.01 | 1.81 | 0 | 24.05 |
| | % ITE | +9.89 | +89.3 | −48.6 | — | — |
| 9 | Amycacin | 17.7 | 3.12 | 2.94 | 0 | 23.76 |

TABLE 7-continued

Effect of the new treatment on the activity of TB drugs, as measured by morphological activity

| No. of group | Drug | Scored sum of area | | | | |
|---|---|---|---|---|---|---|
| | | Breathing lung tissue | Dense lymphocytic infiltrate | Desquamative pneumonia | Polymorpho cellular infiltrate | Total lung tissue |
| 10 | Amycacin + new treatment | 17.32 | 2.98 | 3.51 | 0.07 | 23.88 |
| | % ITE | −2.1 | −4.5 | +19.4 | — | — |
| 12 | Ethambutol | 9.78 | 6.8 | 6.93 | 0.27 | 23.78 |
| 13 | Ethambutol + new treatment | 14.49 | 4.65 | 4.68 | 0.14 | 23.96 |
| | % ITE | +48.14-5 | −31.6 | −32.5 | — | — |
| 14 | Ofloxacin | 7.32 | 6.32 | 10.49 | 0.04 | 24.17 |
| 15 | Ofloxacin + new treatment | 8.95 | 3.47 | 11.18 | 0.42 | 24.02 |
| | % ITE | +22.3 | −45.1 | +6.6 | — | — |

TABLE 8

TB drug classification depending on therapeutic effectiveness of these drugs used in combination with the new treatment

| Damage test | Effect of TB drug used in combination with the new treatment | |
|---|---|---|
| | Potentiate | Attenuate |
| Coefficient of lung weight | Rifampicin Amycacin Rifabutin | Ofloxacin Ethambutol |
| Coefficient of spleen weight | Rifampicin Amycacin Rifabutin | Ofloxacin Ethambutol |
| CFU level in the spleen | Rifampicin Amycacin Rifabutin | Ofloxacin |
| Breathing lung tissue score | Rifabutin Rifampicin | Ofloxacin Ethambutol |
| Dense lymphocytic infiltrate score | Rifabutin Amycacin Rifampicin | Ethambutol |
| Desquamative pneumonia score | Rifabutin Isoniazid Rifampicin | Ofloxacin Ethambutol |

Therefore, the new treatment exhibits a marked, strictly selective inhibiting activity against *Mycobacteria tuberculosis* either sensitive or resistant to current TB drugs. The new treatment is a low toxic agent and causes neither a significant structural and functional damage to vital organs and systems nor irritation of gastrointestinal mucosa.

The new treatment exhibits moderate embryo toxicity, mainly if administered during organogenesis, and has a selective activity depending on individual sensitivity of animals. The new treatment appears to have a teratogenic effect, in the form of non life-threatening skeletal malformations, delay in the ossification of the sternum and extremities, edema, and subcutaneous hemorrhage, only at a dose of 100 mg/kg (five times the therapeutic dose) when administered during organogenesis. It causes no alterations in placenta development and sex formation. Continued administration of the new treatment has no effect on the reproductive function and offspring development in animals.

The new treatment has no allergenic, immunotoxic, and mutagenic properties.

Based on the above data, it is reasonable to conclude that a new medication with higher tuberculostatic activity (200 times as high) and lower toxicity (2.4 times as low) has been developed in comparison with the prototype drug.

When used in combination with other TB drugs (rifabutin, rifampicin, isoniazid, amycacin, and ethambutol), the new treatment increased the therapeutic effectiveness, as compared to monotherapy with the new treatment alone.

The new treatment is stable during storage, and its appearance, physical characteristics, and biological properties are stable for 3 years.

BRIEF DESCRIPTION OF THE DRAWINGS

For a fuller understanding of the invention, reference should be made to the following detailed description, taken in connection with the accompanying drawings, in which:

FIG. 1 is a table showing the effect of the new treatment on therapeutic effectiveness of TB drugs when used in combination (42 days of treatment).

FIG. 2 is a table showing the effect of the new treatment on therapeutic effectiveness of TB drugs when used in combination (42 days of treatment).

DETAILED DESCRIPTION OF THE PREFERRED EMBODIMENTS

The following examples serve to illustrate (without limiting the scope of claims) the most preferable variants of the embodiment of the invention and prove the possibility to prepare the new treatment.

As used herein, a "therapeutically effective amount" refers to that amount of the compound of the invention or other active ingredient sufficient to provide a therapeutic benefit in the treatment or management of tuberculosis or to delay or minimize symptoms associated with tuberculosis.

As used herein, a "therapeutically safe amount" refers to that amount of the compound of the invention or other active ingredient sufficient to induce a positive benefit while concurrently avoiding serious side effects, in particular avoiding unacceptable drug related adverse events, as determined within the scope of sound judgment of a skilled artisan.

A "prophylactically effective amount" refers to that amount of compound of the invention sufficient to result in the prevention, recurrence, or spread of disease. The prophylactically effective amount may refer to the amount sufficient to prevent initial disease, recurrence or spread of the disease or the occurrence of the disease in a patient, including, but not limited, to patients particularly susceptible to the disease, or occurrence of disease in another patient, i.e. spread of disease.

Example 1

The formulation is in tablet dosage form and has the following composition (expressed as percent by weight of the tablet core).
Composition Per Tablet:

|  | % (mg)* | | | |
|---|---|---|---|---|
| Core composition: | | | | |
| 4-thioureido-iminomethylpyridinium perchlorate | 8.0 (23.2) | 50.0 (145.0) | 68.97 (200.0) | 90 (261.0) |
| Colloidal silicon dioxide | 5.1 (14.9) | 2.78 (8.05) | 1.72 (5.0) | 0.56 (1.61) |
| Crosspovidone | 17.9 (51.8) | 9.72 (28.19) | 6.03 (17.50) | 1.94 (5.64) |
| Magnesium stearate | 2.59 (7.5) | 1.39 (4.03) | 0.86 (2.50) | 0.28 (0.81) |
| Povidone | 5.1 (14.9) | 2.78 (8.05) | 1.72 (5.0) | 0.56 (1.61) |
| Microcrystalline cellulose | 61.3 (177.7) | 33.34 (96.68) | 20.69 (60.0) | 6.66 (19.3) |
| Tablet core weight (mg): | 290.0 | 290.0 | 290.0 | 290.0 |
| Coating composition: | | | | |
| Hypromellose E 5 | 0.12 (0.35) | 0.12 (0.35) | 0.12 (0.35) | 0.12 (0.35) |
| Hypromellose E 15 | 2.07 (6.0) | 2.07 (6.0) | 2.07 (6.0) | 2.07 (6.0) |
| Yellow ferric oxide | 0.14 (0.40) | 0.14 (0.40) | 0.14 (0.40) | 0.14 (0.40) |
| Macrogol 6000 | 0.43 (1.25) | 0.43 (1.25) | 0.43 (1.25) | 0.43 (1.25) |
| Talc | 0.35 (1.0) | 0.43 (1.25) | 0.43 (1.25) | 0.43 (1.25) |
| Propylene glycol | 0.17 (0.50) | 0.17 (0.50) | 0.17 (0.50) | 0.17 (0.50) |
| Titanium dioxide | 0.17 (0.50) | 0.17 (0.50) | 0.17 (0.50) | 0.17 (0.50) |
| Coated tablet weight (mg) | 300.0 | 300.0 | 300.0 | 300.0 |

*expressed as percent by weight of the tablet core

Modified Release Tablets 100, 200, 400, 800, and 1000 mg
Composition Per Tablet, mg:

| 4-thioureido-iminomethylpyridinium perchlorate | 100.0 | 200.0 | 400.0 | 800.0 | 1000.0 |
|---|---|---|---|---|---|
| Colloidal silicon dioxide | 1.5 | 3.0 | 6.0 | 12.0 | 15.0 |
| Calcium hydrophosphate | 12.5 | 25.0 | 50.0 | 100.0 | 125.0 |
| Povidone | 2.5 | 5.0 | 10.0 | 20.0 | 25.0 |
| Magnesium stearate | 1.5 | 3.0 | 6.0 | 12.0 | 15.0 |
| Ammonium methacrylate copolymers | 12.5 | 25.0 | 50.0 | 100.0 | 125.0 |
| Talc | 1.5 | 3.0 | 6.0 | 12.0 | 15.0 |
| Microcrystalline cellulose | 17.5 | 35.0 | 70.0 | 140.0 | 175.0 |
| Ethylcellulose | 0.5 | 1.0 | 2.0 | 4.0 | 5.0 |
| Tablet weight (mg) | 150.0 | 300.0 | 600.0 | 1200.0 | 1500.0 |

Enteric Coated Tablets 200, 400, 500, 600, and 800 mg
Composition Per Tablet, mg:

| | Core composition: | | | | |
|---|---|---|---|---|---|
| 4-thioureido-iminomethylpyridinium perchlorate | 200.0 | 400.0 | 500.0 | 600.0 | 800.0 |
| Colloidal silicon dioxide | 5.0 | 10.0 | 12.5 | 15.0 | 20.0 |
| Crosspovidone | 17.50 | 35.0 | 43.75 | 52.5 | 70.0 |
| Magnesium stearate | 2.50 | 5.0 | 6.25 | 7.5 | 10.0 |
| Povidone | 5.0 | 10.0 | 12.5 | 15.0 | 20.0 |
| Microcrystalline cellulose | 60.0 | 120.0 | 150.0 | 180.0 | 240.0 |
| Tablet core weight ± 5% | 290.0 | 580.0 | 725.0 | 870.0 | 1160.0 |
| Coating composition: | | | | | |
| Methacrylic acid-ethyl acrylate copolymers | 16 | 32 | 40 | 48 | 64 |
| Yellow ferric oxide | 2 | 4 | 5 | 6 | 8 |
| Macrogol | 0.75 | 1.5 | 1.875 | 2.25 | 3 |
| Talc | 7 | 14 | 17.5 | 21 | 28 |
| Triethyl acetate | 4.25 | 8.5 | 10.625 | 12.75 | 17 |
| Enteric coated tablet weight (mg): | 320.0 | 640.0 | 800.0 | 960.0 | 1280.0 |

Example 2

The formulation is in solid dosage form: coated granules. The coating is applied to provide stability of composition during storage and enhance the appearance and organoleptic properties.
Coated Granule Dosage Form
Composition Per 100 g:

| | Core composition: | | | | |
|---|---|---|---|---|---|
| 4-thioureido-iminomethylpyridinium perchlorate | 5 | 50 | 70 | 80 | 90 |
| Sucrose | 50.4 | 25.2 | 14 | 8.4 | 2.8 |
| Colloidal silicon dioxide | 3.6 | 1.8 | 1 | 0.6 | 0.2 |
| Povidone | 14.4 | 7.2 | 4 | 2.4 | 0.8 |
| Microcrystalline cellulose | 18 | 9 | 5 | 3 | 1 |
| Ethylcellulose | 3.6 | 1.8 | 1 | 0.6 | 0.2 |
| Granule core weight: | 95 | 95 | 95 | 95 | 95 |
| Coating composition: | | | | | |
| Methacrylic acid copolymers | 3.0 | 3.0 | 3.0 | 3.0 | 3.0 |
| Macrogol | 0.2 | 0.2 | 0.2 | 0.2 | 0.2 |

| | | | | | |
|---|---|---|---|---|---|
| Yellow ferric oxide | 0.2 | 0.2 | 0.2 | 0.2 | 0.2 |
| Talc | 0.85 | 0.85 | 0.85 | 0.85 | 0.85 |
| Triethyl acetate | 0.75 | 0.75 | 0.75 | 0.75 | 0.75 |
| Coated granule weight (mg): | 100 | 100 | 100 | 100 | 100 |

The coating composition (expressed as percent by weight of the granule core) may be as follows:
Methacrylic acid and ethyl acrylate copolymers: 3.0-4.0
Triethyl acetate: 0.8-1.2
Macragol: 0.2-0.4
Talc: 0.9-1.3
Ferric oxide dye: 0.2-0.3.

Example 3

Pills 100, 200, 300, and 400 mg
Composition Per Pill:

| | | | | |
|---|---|---|---|---|
| 4-thioureido-iminomethylpyridinium perchlorate | 100.0 | 200.0 | 300.0 | 400.0 |
| Colloidal silicon dioxide | 2.5 | 5.0 | 10.0 | 10.0 |
| Sucrose | 21.0 | 42.0 | 63.0 | 84.0 |
| Magnesium stearate | 1.2 | 2.4 | 3.6 | 4.8 |
| Povidone | 6.0 | 12.0 | 18.0 | 24.0 |
| Microcrystalline cellulose | 22.0 | 44.0 | 66.0 | 88.0 |
| Macrogol | 1.3 | 2.6 | 3.9 | 5.2 |
| Yellow ferric oxide | 1.0 | 2.0 | 3.0 | 4.0 |
| Talc | 3.5 | 7.0 | 10.5 | 14 |
| Titanium dioxide | 1.5 | 3.0 | 4.5 | 6.0 |
| Coated pill weight (mg): | 160.0 | 320.0 | 480.0 | 640.0 |

Example 4

Capsules 50, 100, 200, 300, and 400 mg
Composition Per Capsule:

| Ingredient name | Unit, mg | | | | | |
|---|---|---|---|---|---|---|
| 4-thioureido-iminomethylpyridinium perchlorate | mg | 50.0 | 100.0 | 200.0 | 300.0 | 400.0 |
| Potato or corn starch | mg | 4.0 | 8.0 | 16.0 | 24.0 | 32.0 |
| Colloidal silicon dioxide | mg | 0.5 | 1.0 | 2.0 | 3.0 | 4.0 |
| Crosspovidone | mg | 2.0 | 4.0 | 8.0 | 12.0 | 16.0 |
| Magnesium or calcium stearate | mg | 0.5 | 1.0 | 2.0 | 3.0 | 4.0 |
| Microcrystalline cellulose | mg | 3.0 | 6.0 | 12.0 | 18.0 | 24.0 |
| Capsule content weight: | mg | 60.0 | 120.0 | 240.0 | 360.0 | 480.0 |
| Gelatin capsule | pcs. | 1 | 1 | 1 | 1 | 1 |

| Ingredient name | Unit, mg | % (mg) | | |
|---|---|---|---|---|
| 4-thioureido-iminomethylpyridinium perchlorate | mg | 75 (180.0) | 83.33 (200.0) | 91.7 (220.0) |
| Potato or corn starch | mg | 13.3 (24.0) | 8.0 (16.0) | 3.6 (8.0) |
| Colloidal silicon dioxide | mg | 1.7 (3.0) | 1.0 (2.0) | 0.45 (1.0) |
| Crosspovidone | mg | 6.7 (12.0) | 4.0 (8.0) | 1.82 (4.0) |
| Magnesium or calcium stearate | mg | 1.7 (3.0) | 1.0 (2.0) | 0.45 (1.0) |
| Microcrystalline cellulose | mg | 10.0 (18.0) | 6.0 (12.0) | 2.73 (6.0) |
| Capsule content weight: | mg | 240.0 | 240.0 | 240.0 |
| Gelatin capsule | pcs. | 1 | 1 | 1 |

Example 5

Suspension Dosage Form 4-thioureido-iminomethylpyridinium perchlorate powder for oral suspension (100 ml vials) 200 mg/5 ml, 300 mg/5 ml, 400 mg/5 ml Composition Per 100 ml:

| Ingredient name | Unit, mg | 200 mg/ 5 ml | 300 mg/ 5 ml | 400 mg/ 5 ml |
|---|---|---|---|---|
| 4-thioureido-iminomethylpyridinium perchlorate | mg | 4,000.0 | 6,000.0 | 8,000.0 |
| Colloidal silicon dioxide | mg | 40.0 | 60.0 | 80.0 |
| β-cyclodextrin | mg | 400.0 | 600.0 | 800.0 |
| Citric acid | mg | 200.0 | 300.0 | 400.0 |
| Povidone | mg | 1,400.0 | 2,100.0 | 2,800.0 |
| Sucrose (or sorbitol) | mg | 3,950.0 | 5,925.0 | 7,900.0 |
| *Vanilla*, apple, or banana flavor | mg | 10.0 | 15.0 | 20.0 |
| Weight of powder for suspension: | mg | 10,000.0 ± 3% | 15,000.0 ± 3% | 20,000.0 ± 3% |

| Ingredient name | Unit, mg | % (mg) | | |
|---|---|---|---|---|
| 4-thioureido-iminomethyl-pyridinium perchlorate | mg | 36 (3600.0) | 40.0 (4000.0) | 44 (4400.0) |
| Colloidal silicon dioxide | mg | 1.19 (43.0) | 1.0 (40.0) | 0.82 (36.0) |
| β-cyclodextrin | mg | 11.94 (430.0) | 10.0 (400.0) | 8.18 (360.0) |
| Citric acid | mg | 5.83 (210.0) | 5.0 (200.0) | 4.09 (180.0) |
| Povidone | mg | 41.39 (1490.0) | 35.0 (1400.0) | 28.64 (1260.0) |
| Sucrose (or sorbitol) | mg | 116.94 (4210.0) | 98.8 (3950.0) | 80.91 (3560.0) |
| *Vanilla*, apple, or banana flavor | mg | 0.31 (11.0) | 0.25 (10.0) | 0.2 (9.0) |
| Weight of powder for suspension | mg | 10,000.0 | 10,000.0 | 10,000.0 |
| For suspension: | | | | |
| Purified water | mg | 90,000.0 | 90,000.0 | 90,000.0 |
| Suspension weight: | mg | 100,000.0 | 100,000.0 | 100,000.0 |

All components and ratios of components are determined experimentally and are optimal, which makes it possible to prepare a TB treatment meeting the requirements of the state pharmaceutical authorities.

Example 6

Rectal Suppositories 50, 100, 200, and 300 mg

| Ingredient name | Unit, mg | | | | |
|---|---|---|---|---|---|
| 4-thioureido-iminomethylpyridinium perchlorate | mg | 50.0 (46.0-54.0) | 100.0 (95.0-105.0) | 200.0 (190.0-210.0) | 300.0 (285.0-315.0) |
| β-cyclodextrin | mg | 40.0 | 80.0 | 160.0 | 240.0 |
| Glycerol | mg | 10.0 | 20.0 | 40.0 | 60.0 |
| Macragol | mg | 100.0 | 200.0 | 400.0 | 600.0 |
| Witepsol suppository basis | mg | 400.0 | 800.0 | 1,600.0 | 2,400.0 |
| Suppository weight | mg | 600.0 (570.0-630.0) | 1,200.0 (1,140.0-1,260.0) | 2,400.0 (2,280.0-2,520.0) | 3,600.0 (3,420.0-3,780.0) |

Example 7

Target Additives: 4-Thioureido-Iminomethylpyridinium Perchlorate 44.5% w/w

Sieved powders of 4-thioureido-iminomethylpyridinium perchlorate at the level of 70.0 g, microcrystalline cellulose 5.0 g, colloidal silicon dioxide 1.0 g, and ethylcellulose of 1.0 g are put into a mixer and mixed for 5-10 min at the rate of 25 rpm. To the resulting mixture is added an aqueous solution of povidone and sucrose, which consists of 4.0 g of povidone, 14.0 g of sucrose, and 28 ml of water; the wet mass is passed through a granulator; the wet granules are rolled to make them of desired size and dried at 40-45° C. until the residual moisture content in granules is 1.5-4.5%. The resulting granule cores are passed through 1.0-3.0 mm sieves. The granule cores of 1.0-3.0 mm in diameter are film-coated with suspension prepared on the basis of methacrylic acid copolymers.

A total of 0.85 g of talc and 0.2 g of ferric oxide dye are mixed with 0.2 g of macrogol and 5 ml of water to obtain a cream-like consistency and then are mixed with 3.0 g of copolymer of methacrylic acid dispersed in 15 ml of water. The granule cores, when heated up to 45-50° C., are film-coated, with constant mixing and simultaneous drying with hot air to obtain 100.0 g of granules with uniform coating. The granules obtained meet the requirements of the state pharmaceutical authorities.

Example 8

Target Additives: 4-Thioureido-Iminomethylpyridinium Perchlorate 11.0% w/w

Target additives are the same as in Example 6, although amounts of components are different.

Sieved powders of 4-thioureido-iminomethylpyridinium perchlorate of 90.0 g, microcrystalline cellulose of 1.0 g, colloidal silicon dioxide of 0.2 g, and ethylcellulose of 0.2 g are put into a mixer and mixed for 5-10 min at the rate of 25 rpm. To the resulting mixture is added an aqueous solution of povidone and sucrose, which consists of 0.8 g of povidone, 2.8 g of sucrose, and 6 ml of water; the wet mass is passed through a granulator; the wet granules are rolled to make them of desired size and dried at 40-45° C. until the residual moisture content in granules is 1.5-4.5%. The resulting granule cores are passed through 1.0-3.0 mm sieves. The granule cores of 1.0-3.0 mm in diameter are film coated with suspension prepared on the basis of methacrylic acid copolymers.

A total of 0.85 g of talc and 0.2 g of ferric oxide dye are mixed with 0.2 g of macrogol and 5 ml of water to obtain a cream-like consistency and then are mixed with 3.0 g of copolymer of methacrylic acid dispersed in 15 ml of water. When the granule cores are heated up to 45-50° C., film coating is performed, with constant mixing and simultaneous drying with hot air to obtain 100.0 g of granules with uniform coating. The granules obtained are of yellow or red colour, are round or irregular in shape, and meet the requirements of the state pharmaceutical authorities.

Example 9

Target Additives: 4-Thioureido-Iminomethylpyridinium Perchlorate 100% w/w

Target additives are the same as in Example 6, although amounts of components are different. Sieved powders of 4-thioureido-iminomethylpyridinium perchlorate of 50.0 g, microcrystalline cellulose of 9.0 g, colloidal silicon dioxide of 1.8 g, and ethylcellulose of 1.8 g are put into a mixer and mixed for 5-10 min at the rate of 25 rpm. To the resulting mixture is added an aqueous solution of povidone and sucrose, which consists of 7.2 g of povidone, 25.2 g of sucrose, and 50 ml of water; the wet mass is passed through a granulator; the wet granules are rolled to make them of desired size and dried at 40-45° C. until the residual moisture content in granules is 1.5-4.5%. The resulting granule cores are passed through 1.0-3.0 mm sieves. The granule cores of 1.0-3.0 mm in diameter are film coated with suspension prepared on the basis of methacrylic acid copolymers. A total of 0.85 g of talc and 0.2 g of ferric oxide dye are mixed with 0.2 g of macrogol and 5 ml of water to obtain a cream-like consistency and then are mixed with 3.0 g of copolymer of methacrylic acid dispersed in 15 ml of water.

When the granule cores are heated up to 45-50° C., film coating is performed, with constant mixing and simultaneous drying with hot air to obtain 100.0 g of granules with uniform coating. The granules obtained meet the requirements of the state pharmaceutical authorities.

Example 10

Powders of 4-thioureido-iminomethylpyridinium perchlorate, colloidal silicon dioxide, crosspovidone, magnesium stearate, povidone, microcrystalline cellulose, hypromellose, talc, macrogol, propylene glycol, titanium dioxide, and yellow ferric oxide, all taken in required amounts as in Example 1, are independently sifted through sieves.

To prepare a humectant, estimated amounts of purified cold water and povidone are introduced into a reactor and mixed for 30 min at 60° C. until a clear, homogenous solution of light-yellow colour is obtained. Estimated amounts of 4-thioureido-iminomethylpyridinium perchlorate and microcrystalline cellulose are put into a mixer and mixed for 15 min, and then a humectant is added and mixed for at least 15 min until a uniform homogenous mass is obtained. The mass is subjected to wet granulation in a fluidized bed. Wet granulated material is dried for 20 min at 0.2 mPa and 55±2° C. until the residual moisture content is 1.0-2.0. The dried granulated material is subjected to dusting and dry granulation and is poured into the vibrosieve hopper; then the dried granulated material and dusting powder (aerosil, crosspovidone, and magnesium stearate) are put into the mixer, avoiding dust generation; the semi-product is mixed for 15 min to obtain mass for tabletting. The resulting mass is compressed in the tablet press.

Tablet cores are film coated with aqueous suspension containing hypromellose mixture, yellow ferric oxide, macrogol, talc, propylene glycol, and titanium dioxide to obtain the new treatment as in claim 1.

Example 11

Target Additives: 4-Thioureido-Iminomethylpyridinium Perchlorate 20.0% w/w

Sieved powders of 4-thioureido-iminomethylpyridinium perchlorate of 200.0 g, dry potato starch of 16.0 g, microcrystalline cellulose of 12.0 g, crosspovidone of 8.0 g, colloidal silicon dioxide of 2.0 g, and magnesium stearate of 2.0 g are put into a mixer and mixed for 5-10 min at the rate of 50 rpm until a uniform distribution of the active ingredient is obtained. The moisture content in the mixture is 1-3%. The resulting mass is put into automatic capsule filling machines and filled into capsules. Loose dust adhered to the capsules is removed, and the capsules are packed either in plastic bottles or in blister packs. The yield is 1,000 capsules of the new treatment with a total weight of 240.0 g or 0.24 g±10%, each capsule contains 0.20 g±10% of active ingredient. The capsules obtained meet all requirements for pharmaceutical products.

Example 12

Target Additives: 4-Thioureido-Iminomethylpyridinium Perchlorate 33.3% w/w

Target additives are in the same amount as in Example 1, but corn starch is taken instead of potato starch and 4-thioureido-iminomethylpyridinium perchlorate is taken in amount of 180 g. The yield is 1,000 capsules of the new treatment with a total weight of 240.0 g or 0.24 g±10%, each capsule contains 0.20 g±10% of active ingredient. The capsules obtained meet all requirements for pharmaceutical products.

Example 13

Target Additives: 4-Thioureido-Iminomethylpyridinium Perchlorate 9.1% w/w

Target additives are in the same amount as in Example 1, but calcium stearate is taken instead of magnesium stearate and 4-thioureido-iminomethylpyridinium perchlorate is taken in amount of 220 g.

The yield is 1,000 capsules of the new treatment with a total weight of 240.0 g or 0.24 g±10%, each capsule contains 0.20 g±10% of active ingredient. The capsules obtained meet all requirements for pharmaceutical products.

Example 14

Manufacture of suppositories involves a molding process. Amounts of ingredients are calculated to have a yield of 100 suppositories. A total of 5.0 g of 4-thioureido-iminomethylpyridinium perchlorate, 4.0 g of 3-cyclodextrin, and 1.0 g of glycerol are put into a miller and are ground for 30 min. The resulting suspension is mixed in a reactor with 15.0 g of suppository base and macrogol heated up to 45° C. The resulting concentrate is cooled and then is ground for 3 h in a three-roller ointment grinder to obtain a required dispersion of the new treatment. The finished concentrate is mixed with 35.0 g of suppository base and macrogol at 48° C. until a uniform mass is obtained. The resulting mixture is poured into molds and packed. The yield is 100 suppositories meeting the following requirements: mean mass and uniformity of mass: 0.60 g±5%; melting temperature: not higher than 37° C.; amount of 4-thioureido-iminomethylpyridinium perchlorate per suppository: 0.05 (0.046-0.054).

Example 15

Sieved powders of 4-thioureido-iminomethylpyridinium perchlorate of 4.0 g, β-cyclodextrin of 0.40 g, and povidone of 1.40 g are put into a ball mill and are ground for 3 h. To the resulting complex, sieved powders of sucrose of 3.95 g, citric acid of 0.20 g, and vanilla flavour of 0.01 g are added and ground for 1 h. The ground powder is put into a mixer and is mixed with 0.04 g of colloidal silicon dioxide for 5-10 min at the rate of 50 rpm until a uniform mixture is obtained. The resulting mixture is automatically filled into vials, 10.0 g per each vial. Vials are hermetically sealed with caps and are packed into a box, with a 5 ml spoon. The obtained suspension meets the following requirements: variation of the vial content: 9.7 g to 10.3 g; water content in powder: not more than 2%; pH: 5-8; sedimentation stability of suspension: not less than 24 h.

For oral administration, dissolve the powder with 90 ml of water to the mark and use 5 ml spoon. Each 100 ml of suspension contains 20 doses, each containing 200 mg of active ingredient 4-thioureido-iminomethylpyridinium perchlorate.

Example 16

Combined Preparation in the Form of Capsules 100 mg+100 Mg, 150 mg+200 mg (Rifampicin+Perchlozone)
Composition Per Capsule:

| Ingredient name | Unit, mg | | |
|---|---|---|---|
| 4-thioureido-iminomethylpyridinium perchlorate | mg | 100.0 | 200.0 |
| Rifampicin | mg | 100.0 | 150.0 |
| Potato or corn starch | mg | 38.0 | 76.0 |
| Colloidal silicon dioxide | mg | 1.0 | 2.0 |
| Crosspovidone | mg | 4.0 | 8.0 |
| Magnesium or calcium stearate | mg | 1.0 | 2.0 |
| Microcrystalline cellulose | mg | 6.0 | 12.0 |
| Capsule weight: | mg | 250.0 | 450.0 |
| Gelatin capsule | pcs | 1 | 1 |

What is claimed is:
1. A composition, comprising:
a therapeutically effective and safe amount of an active ingredient, wherein the active ingredient is 4-thioureido-iminomethylpyridinium perchlorate or a combination of 4-thioureido-iminomethylpyridinium perchlorate and other anti-tubercular drugs;

wherein 4-thioureido-iminomethylpyridinium perchlorate is in an amount of 8.0% to 90.0% w/w;
a combination of pharmaceutically acceptable excipients, wherein the combination of pharmaceutically acceptable excipients are:
colloidal silicon dioxide in an amount of 0.56% to 5.1% w/w;
crosspovidone in an amount of 1.94% to 17.9% w/w;
magnesium stearate in an amount of 0.28% to 2.59% w/w;
povidone in an amount of 0.56% to 5.1% w/w;
microcrystalline cellulose in an amount of 6.66% to 61.3% w/w;
wherein the amounts are percent by weight of the pharmaceutical composition.

2. The composition of claim 1, wherein 4-thioureido-iminomethylpyridinium perchlorate is between 10 mg and 1000 mg.

3. The composition of claim 1, wherein the povidone is in an amount of 0.9% to 5.1% w/w of the composition;

the microcrystalline cellulose is in an amount of 6.66% to 18.0% w/w of the composition; and the colloidal silicon dioxide is in an amount of 0.56% to 3.6% w/w of the composition.

4. The composition of claim 1, further comprising:

a coating comprising copolymers of methacrylic acid and ethyl acrylate, triethyl citrate, macragol, talc, and ferric oxide dye, wherein the methacrylic acid and ethyl acrylate copolymer is in an amount of 3.0% to 4.0% w/w of the composition;

triethyl acetate is in an amount of 0.8% to 1.8% w/w of the composition;
macragol is in an amount of 0.2% to 0.4% w/w of the composition;

talc is in an amount of 0.9% to 1.3% w/w of the composition; and ferric oxide dye is in an amount of 0.2% and 0.3% w/w of the composition.

5. The composition of claim 1, further comprising:
at least one additional tuberculosis agent in an amount of not more than 90% w/w of the composition.

6. The composition of claim 5, wherein the additional tuberculosis agents are selected from the group consisting of isoniazid, pyrazinamid, rifampicin, rifabutin, amikacin, ethambutol, and fluoroquinolone antibiotic.

7. The composition of claim 6, wherein the 4-thioureido-iminomethylpyridinium perchlorate is between 10 mg and 1000 mg; and the isoniazid is at between 10 mg and 500 mg, the rifampicin is at between 10 mg and 667 mg, the rifabutin is at between 8.5 mg and 284 mg, the amikacin is at between 20 mg and 667 mg, the ethambutol is at between 20 mg and 667 mg, or the ofloxacin is at between 20 mg and 667 mg.

8. The composition of claim 1, wherein the composition is in a form selected from the group consisting of film-coated tablets, combined tablets, capsules, granules, suppositories, and suspensions.

9. A method of treating and preventing pulmonary and extrapulmonary tuberculosis, the method comprising the step of:

administering a composition in a therapeutically effective amount to a patient in need thereof, wherein the composition comprises:

a therapeutically safe and effective amount of 4-thioureido-iminomethylpyridinium perchlorate or a combination of 4-thioureido-iminomethylpyridinium perchlorate and other anti-tubercular drugs;

wherein 4-thioureido-iminomethylpyridinium perchlorate is in an amount of 8.0% to 90.0% w/w; and a combination of pharmaceutically acceptable excipients;

colloidal silicon dioxide in an amount of 0.56% to 5.1% w/w;

crosspovidone in an amount of 1.94% to 17.9% w/w;

magnesium stearate in an amount of 0.28% to 2.59% w/w;

povidone in an amount of 0.56% to 5.1% w/w;

microcrystalline cellulose in an amount of 6.66% to 61.3% w/w;

wherein the amounts are percent by weight of the pharmaceutical composition.

10. The method of claim 9, wherein the composition is administered by oral or parenteral route.

11. The method of claim 9, wherein 4-thioureido-iminomethylpyridinium perchlorate is administered at between 10 mg/kg and 30 mg/kg.

12. The method of claim 9, wherein the 4-thioureido-iminomethylpyridinium perchlorate is administered in a single daily dose of 20 mg/kg.

13. The method of 9, further comprising administering at least one additional tuberculosis agent, wherein the at least one additional tuberculosis agent is selected from the group consisting of isoniazid, pyrazinamid, rifampicin, rifabutin, amycacin, ethambutol, and fluoroquinolone antibiotic.

14. The method of claim 13, wherein the isoniazid is administered at between 10 mg/kg and 15 mg/kg, the rifampicin is administered at between 10 mg/kg and 20 mg/kg, the rifabutin is administered at 8.5 mg/kg, the amikacin is administered at 20 mg/kg, the ethambutol is administered at 20 mg/kg, or the ofloxacin is administered at 20 mg/kg.

15. The composition of claim 1, further comprising:

a coating covering the 4-thioureido-iminomethylpyridinium perchlorate and the combination of pharmaceutically acceptable excipients, wherein the coating comprises:

hypromellose E5 in an amount of 0.12% w/w of the composition;

hypromellose E15 in an amount of 2.07% w/w of the composition;

yellow ferric oxide in an amount of 0.14% w/w of the composition;

macrogol 6000 in an amount of 0.43% w/w of the composition;

talc in an amount of 0.35% w/w of the composition;

propylene glycol in an amount of 0.17% w/w of the composition; and titanium dioxide in an amount of 0.17% w/w of the composition.

* * * * *